(12) United States Patent
Otsubo et al.

(10) Patent No.: US 9,283,125 B2
(45) Date of Patent: Mar. 15, 2016

(54) DISPOSABLE WEARING ARTICLE

(75) Inventors: Toshifumi Otsubo, Kagawa (JP);
Tatsuya Hashimoto, Kagawa (JP);
Mariko Yamashita, Kagawa (JP);
Etsuko Kudo, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 13/392,906

(22) PCT Filed: Aug. 31, 2010

(86) PCT No.: PCT/JP2010/005357
§ 371 (c)(1),
(2), (4) Date: Feb. 28, 2012

(87) PCT Pub. No.: WO2011/024489
PCT Pub. Date: Mar. 3, 2011

(65) Prior Publication Data
US 2012/0165774 A1 Jun. 28, 2012

(30) Foreign Application Priority Data

Aug. 31, 2009 (JP) ................................. 2009-201056
Jun. 11, 2010 (JP) ................................. 2010-134547

(51) Int. Cl.
*A61F 13/15* (2006.01)
*A61F 13/20* (2006.01)
*A61F 13/514* (2006.01)

(52) U.S. Cl.
CPC ..... *A61F 13/51464* (2013.01); *A61F 13/51401* (2013.01); *A61F 13/51476* (2013.01)

(58) Field of Classification Search
CPC .................... A61F 13/51401; A61F 13/51464; A61F 13/51476

USPC ................................ 604/365–367, 370, 384
See application file for complete search history.

(56) References Cited

U.S. PATENT DOCUMENTS 6,461,338 B1  10/2002  Shimoe et al.
6,503,236 B1   1/2003  Uitenbroek et al.
(Continued)

FOREIGN PATENT DOCUMENTS

JP          1122006       8/1989
JP        2001070345 A    3/2001
(Continued)

OTHER PUBLICATIONS

International Search Report and Written opinion for PCT/JP2010/005357 dated Nov. 9, 2010.
(Continued)

*Primary Examiner* — Jason Flick
*Assistant Examiner* — Aundria Hairell
(74) *Attorney, Agent, or Firm* — Hauptman Ham, LLP

(57) ABSTRACT

In a disposable wearing article, a first waist region is elasticized and formed of an inner sheet and an outer sheet. The non-skin-facing side of the outer sheet is formed substantially over its entire area with a plurality of thermocompression-bonded spots regularly and intermittently arranged at predetermined intervals. The outer sheet has non-thermocompressed regions surrounded by a plurality of thermocompression-bonded spots. A fibrous layer lying at least on the outer surface of said outer sheet is formed of thermal adhesive crimped fibers which are bonded together by thermocompression-bonding treatment in the thermocompression-bonded spots. The outer sheet and the inner sheet are bonded to each other by adhesive applied on at least one of respective opposite surfaces thereof so that the crimped fibers in the non-thermocompressed regions may protrude outward in a thickness direction of the outer sheet as the inner sheet contracts in the direction of the transverse axis Q.

19 Claims, 11 Drawing Sheets

(56) References Cited

U.S. PATENT DOCUMENTS

| | | |
|---|---|---|
| 2002/0156444 A1 | 10/2002 | Otsubo |
| 2004/0067709 A1* | 4/2004 | Kishine et al. ............... 442/327 |
| 2009/0169802 A1* | 7/2009 | Miyamura et al. ............ 428/103 |

FOREIGN PATENT DOCUMENTS

| | | |
|---|---|---|
| JP | 3340032 | 10/2002 |
| JP | 2003306858 A | 10/2003 |
| JP | 2003534041 A | 11/2003 |
| JP | 2005211676 A | 8/2005 |
| JP | 2005224618 A | 8/2005 |
| JP | 2009-001930 A | 1/2009 |
| WO | 9802610 A1 | 1/1998 |

OTHER PUBLICATIONS

Extended European Search Report issued May 13, 2013 corresponds to EP Patent application No. 10811543.7.

* cited by examiner (a)

(b)

DISPOSABLE WEARING ARTICLE

RELATED APPLICATIONS

The present application is a National Phase of International Application Number PCT/JP2010/005357, filed Aug. 31, 2010, and claims priority from, Japanese Application Number 2009-201056, filed Aug. 31, 2009 and Japanese Application Number 2010-134547, filed Jun. 11, 2010.

TECHNICAL FIELD

The present disclosure relates to disposable wearing articles and more particularly to disposable wearing articles having improved texture and flexibility such as disposable diapers, disposable toilet-training pants, disposable incontinent pants or disposable menstruation napkins or the like.

RELATED ART

Conventionally, disposable diapers using bulky fiber layers to achieve desired flexibility are known. For example, PATENT DOCUMENT 1 (JP 3340032 B1) discloses a bulky fibrous non-woven fabric used as an outer sheet of a disposable diaper wherein this bulky fibrous non-woven fabric comprises an inelastic outer sheet lying on a non-skin-facing side and an elastically stretchable and contractible inner sheet lying on a skin-facing side thermocompression-bonded to each other.

In this diaper, non-thermocompressed regions each defined by a plurality of intermittently arranged thermocompression-bonded spots form wrinkles protruding toward the outer sheet in the thickness direction to provide flexibility higher than that provided by the sheet material having smooth surface.

However, in this diaper of prior art, the diaper is formed on its outer surface with many large and small wrinkles which may cause relatively rough feel experienced by the wearer. In addition to this, such wrinkles may have a problem from the standpoint of appearance.

CITATION LIST

Patent Literature

[PATENT DOCUMENT 1] JP 3340032 B1

SUMMARY

A disposable wearing article in accordance with one or more embodiments of the present invention has a longitudinal axis extending in a longitudinal direction, a transverse axis orthogonal to said longitudinal axis and extending in a transverse direction, and comprises a skin-facing side, a non-skin-facing side, a first waist region corresponding to one of front and rear waist regions, a second waist region corresponding to the other of the front and rear waist regions and a crotch region extending between the first and second waist regions, wherein, at least one of the first and second waist regions as a whole, or in only its part lying adjacent a waist-opening, is elasticized and formed of an inner sheet defining the skin-facing side and an outer sheet defining the non-skin-facing side and the side facing away from the wearer's skin of the outer sheet is formed substantially over its entire area with a plurality of thermocompression-bonded spots regularly and intermittently arranged at intervals.

The outer sheet has non-thermocompressed regions surrounded by the plurality of thermocompression-bonded spots; the outer sheet is provided with a fibrous layer at least on the outer surface thereof and being formed of thermal adhesive crimped fibers; the crimped fibers are bonded together by thermocompression-bonding treatment in the thermocompression-bonded spots; the outer sheet and the inner sheet are bonded to each other by adhesive applied on at least one of respective opposite surfaces thereof; and the crimped fibers in the non-thermocompressed regions are arranged to protrude outward in a thickness direction of the outer sheet as the inner sheet contracts in the transverse direction.

DETAILED DESCRIPTION OF THE PREFERRED EMBODIMENTS

<First Embodiment>

Figure 1:
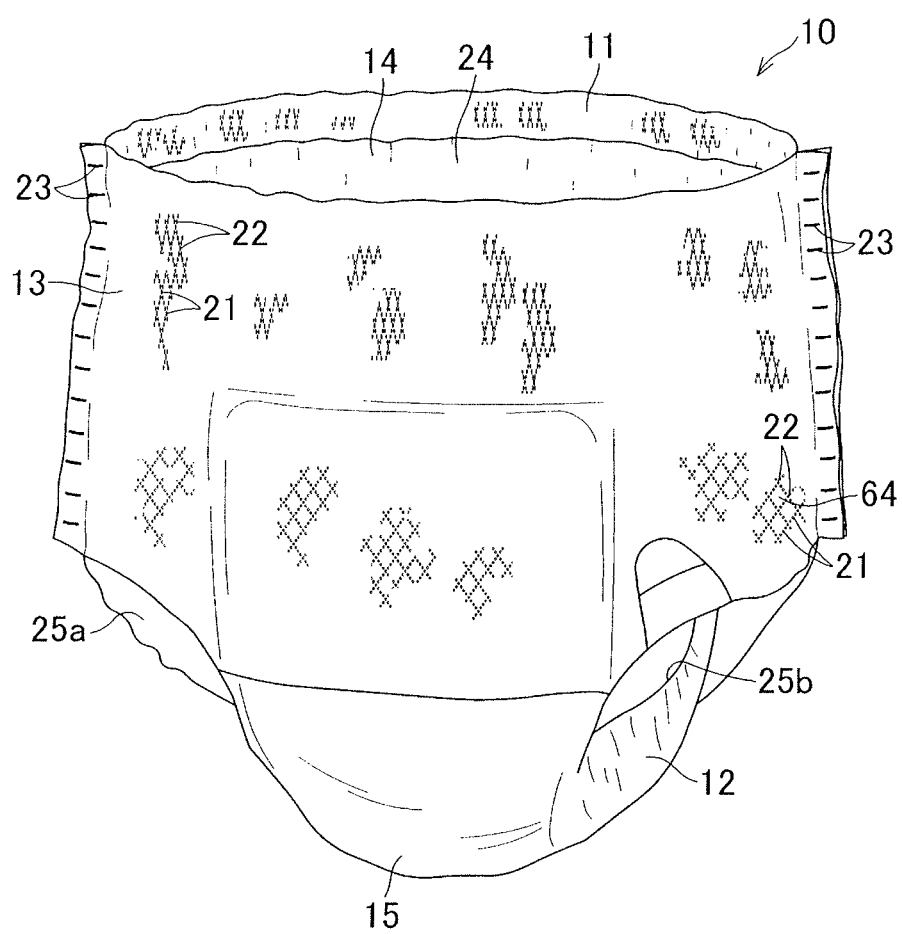
FIG. 1 is a perspective view of a diaper according to a first embodiment of the present invention.
Figure 2:
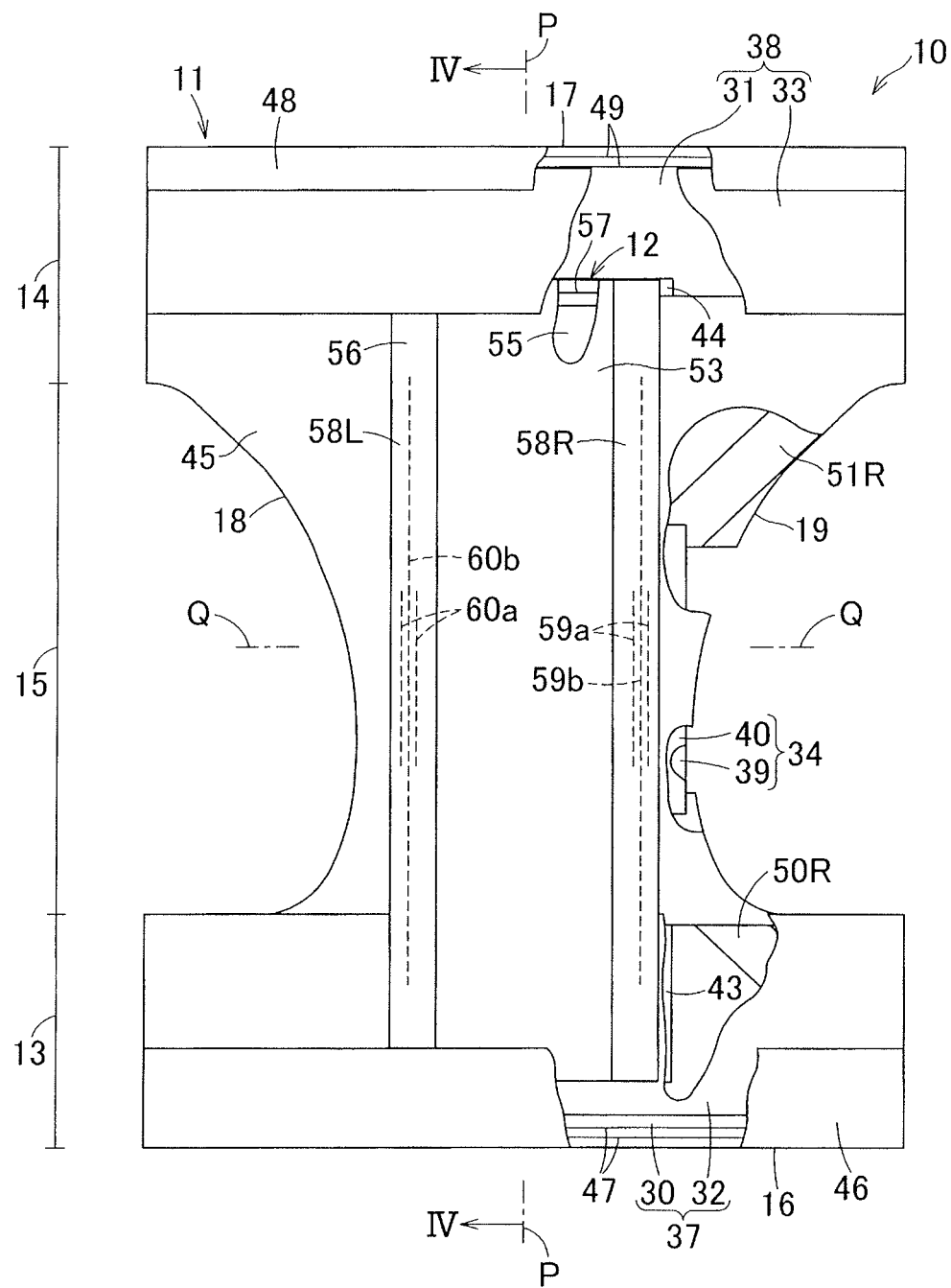
FIG. 2 is a partially cutaway plan view of the diaper as flatly developed.
Figure 3:
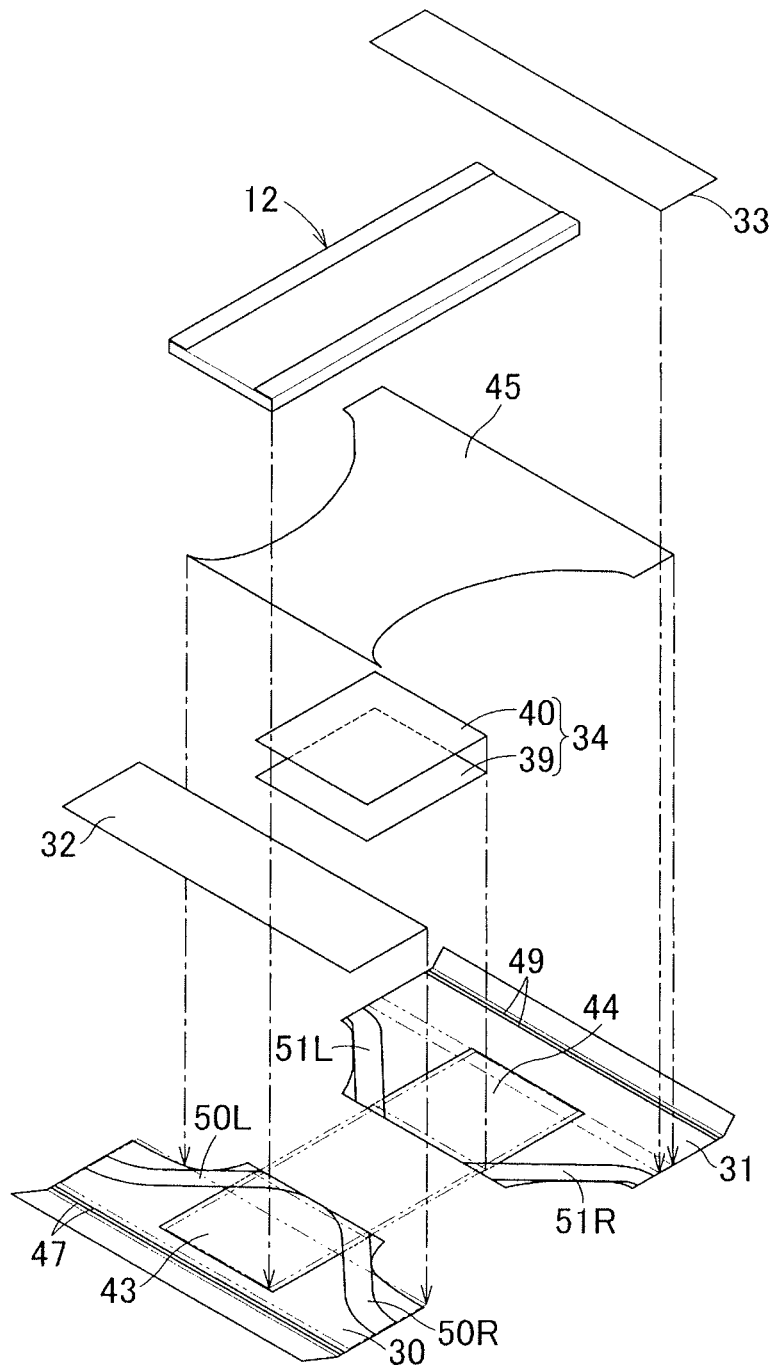
FIG. 3 is an exploded perspective view of the diaper.
Figure 4:
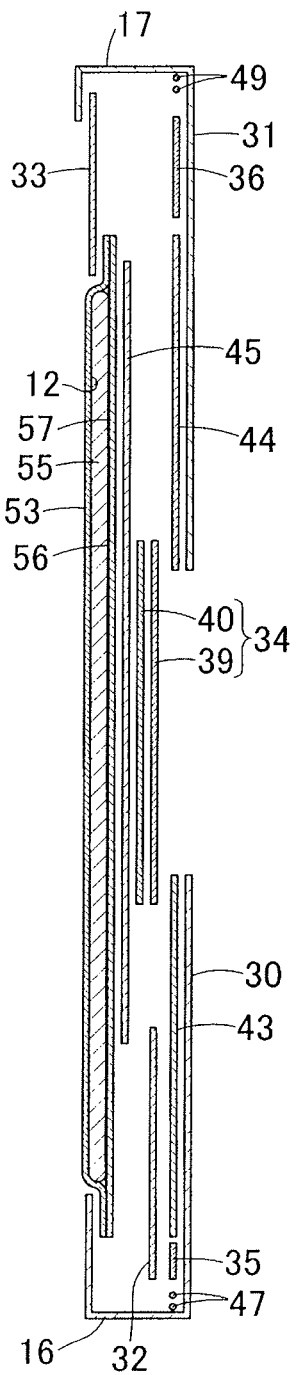
FIG. 4 is a schematic sectional view taken along the line IV-IV in FIG. 2.

Referring now to FIGS. 1 to 4, the diaper 10 is symmetric about the longitudinal axis P. The diaper 10 has a skin-facing side and a non-skin-facing side and basically comprises a chassis 11 defining a contour of the diaper 10 and a liquid-absorbent structure 12 lying on the skin-facing side of the chassis.

More specifically, the diaper 10 has a front waist region 13, a rear waist region 14, a crotch region 15 extending between the front and rear waist regions 13, 14, front and rear ends 16, 17 opposed to each other in a longitudinal direction defined by a longitudinal axis P and extending in a transverse direction defined by a transverse axis Q, and side edges 18, 19 opposed to each other in the transverse direction and extending in the longitudinal direction.

The diaper 10 is formed on its outer surface with a plurality of substantially circular thermocompression-bonded spots (debossed spots) arranged intermittently in given directions to lie in rows and columns intersecting with each other and to define the first and second thermocompression-bonding lines 21, 22. These first and second thermocompression-bonding lines 21, 22 cooperate with each other to create a quilt-like plaid or crisscross pattern.

In the crotch region 15, the side edges 18, 19 concavely curve inward so that the side edges 18, 19 may fit to the wearer's skin around the wearer's thighs. The front waist region 13 and the rear waist region 14 are joined together along the respective side edges by side seams 23 arranged intermittently in the direction defined by the longitudinal axis P along the respective side edges. Thereupon, a waist-opening 24 and a pair of leg-openings 25a, 25b are formed.

The chassis 11 comprises a substantially hexagonal first outer sheet 30 defining the front waist region 13 and a part of the crotch region 15 and a substantially trapezoidal second outer sheet 31 defining the rear waist region 14 and a part of the crotch region 15, each outer sheet lying on the non-skin-facing side, a first inner sheet 32 extending across the front waist region 13 in the transverse direction and bonded to the skin-facing side of the first outer sheet 30, a second inner sheet 33 extending across the rear waist region 14 in the transverse direction and bonded to the skin-facing side of the second outer sheet 31 and a substantially rectangular intermediate sheet 34 extending between the first and second outer sheets 30, 31 to define a middle section of the crotch region 15.

The first outer sheet 30 and the first inner sheet 32 are bonded to each other by first adhesive 35 to form a first laminated sheet 37. The second inner sheet 33 has a width dimension smaller than that of the first inner sheet 32. The second outer sheet 31 and the second inner sheet 33 are bonded to each other by second adhesive 36 to form a second laminated sheet 38. The intermediate sheet 34 comprises a substantially rectangular fibrous non-woven fabric sheet 39 lying on the non-skin-facing side and a moisture-pervious but liquid-impervious plastic sheet 40 which is almost the same as the fibrous non-woven fabric sheet 39 in shape as well as in size. These fibrous non-woven fabric sheet 39 and plastic sheet 40 are bonded to each other by hot melt adhesive (not shown).

The chassis 11 further includes graphic display films 43, 44 made of plastic material laid on the respective non-skin-facing sides of the front and rear waist regions 13, 14 to extend in respective middle regions of these waist regions 13, 14 as viewed in the transverse direction and printed with externally visible graphics or the like (not shown) and a fixing sheet 45 made of a fibrous non-woven fabric extending on the skin-facing side of the chassis 11 across the crotch region 15 further into the front and rear waist regions 13, 14. The fixing sheet 45 has a width dimension larger than that of the intermediate sheet 34 and entirely covers the skin-facing side of the intermediate sheet 34.

Along the front end 16 of the front waist region 13, the first outer sheet 30 is folded back inward to form a front end flap 46 which contains, in turn, a first waist elasticizing element 47 consisting of two elastomer strands attached to the front end flap 46 under tension in a contractible manner. In a similar way, along the rear end 17 of the rear waist region 14, the second outer sheet 31 is folded back inward to form a rear end flap 48 which contains, in turn, a second waist elasticizing element 49 consisting of two elastomer strands attached to the rear end flap 48 under tension in a contractible manner.

The side edges of the crotch region 15 are provided along the segments thereof adjacent to the front waist region 13 (i.e., front half peripheral edges of the respective leg-openings) with elastic elements 50R, 50L formed of elastomeric tape attached under tension in contractible manner to the inner surface of the first outer sheet 30. In a similar manner, the side edges of the crotch region 15 are provided along the segments thereof adjacent to the rear waist region 14 (i.e., rear half peripheral edges of the respective leg-openings) with elastic elements 51R, 51L each comprising elastomeric tapes attached under tension in a contractible manner to the inner surface of the second outer sheet 31. The fixing sheet 45 is attached to the respective outer surfaces of these elastic elements 50R, 50L and 51R, 51L in a manner that the elastic elements 50R, 50L associated with the front half peripheral edges of the respective leg-openings may be partially covered and the elastic elements 51R, 51L associated with the rear half peripheral edges of the respective leg-openings may be fully covered with the fixing sheet 45, respectively.

The first and second outer sheets 30, 31 are formed of a fibrous non-woven fabric. The first and second outer sheets 30, 31 may consist of two or more layers and, in this case, the outermost fibrous layers of the respective outer sheets 30, 31 are preferably formed of crimped spun bonded filament fibers. While the first and second outer sheets 30, 31 including the crimped fibers naturally have stretch properties, it is possible to form the first and second outer sheets 30, 31 of a fibrous non-woven fabric having the stretch properties lower than that of the first and second inner sheets 32, 33. In a preferred embodiment, the first and second outer sheets 30, 31 have an elastic stretch percentage in a range of 100 to 150% and the first and second inner sheets 32, 33 have an elastic stretch percentage in a range of 150 to 300%. It is also possible to regulate a percentage of crimp and a blend ratio of the crimped fibers and thereby to form the first and second outer sheet 30, 31 of a fibrous non-woven fabric substantially having no elastic stretch/contraction properties.

The first and second inner sheets 32, 33 are formed of an elastically stretchable air-through non-woven fabric (of staple fibers) or a spun bonded fibrous non-woven fabric. The intermediate sheet 34 and the fixing sheet 45 may be formed of a spun bonded non-woven fabric of crimped fibers as the first and second outer sheets 30, 31 are, or of an elastically non-stretchable air-through fibrous non-woven fabric or the like. The outer surface of the intermediate sheet 34 may be subjected to the thermocompression-bonding treatment as the first and second outer sheets 30, 31 are, or may not be subjected to such treatment.

The liquid-absorbent structure 12 is provided in the form of a vertically long rectangle contoured by front and rear ends and side edges extending orthogonally to the front and rear ends and extending across the crotch region 15 further into the front and rear waist regions 13, 14. The liquid-absorbent structure 12 comprises a liquid-pervious top-sheet 53 lying on the skin-facing side, a liquid-absorbent core assembly 55 formed of a liquid-absorbent core comprising mixture of fluff pulp fibers and superabsorbent polymer particles and covered with a liquid-dispersant sheet (not shown), a wrapping sheet 56 lying on the non-skin-facing side and adapted to cover the liquid-absorbent core assembly 55 completely, and a leakage-barrier sheet 57 made of plastic material sandwiched between the liquid-absorbent core assembly 55 and the cover sheet 56.

The cover sheet 56 has opposite lateral portions extending in the transverse direction beyond the opposite side edges of the liquid-absorbent core assembly 55. These lateral portions are partially folded back inward to form a pair of sleeve-like side flaps 58R, 58L extending in the longitudinal direction and respectively containing therein elastic elements 59, 60 each comprising three elastomeric tapes extending in the longitudinal direction and attached in contractible manner to the side flaps 58R, 58L by hot melt adhesive. Of the respective elastic elements 59, 60, the outer side elastic tapes 59a, 60a are allocated in the middle of the crotch region 15 and cooperate with the first and second leg-surrounding elastic elements 50R, 50L, 51R, 51L to form elastic belts extending along the wearer' inguinal region. Of the elastic elements 59, 60, the respective central elastic tapes 59b, 60b extend within the respective side flaps 58R, 58L into the front and rear waist regions 13, 14 and the lateral portions of the cover sheet 56 are spaced from the top-sheet 53 under contraction of these elastic members to form barrier- or gasket-cuffs adapted to prevent body waste from leaking sideway.

The non-skin-facing side of the liquid-absorbent structure 12 is entirely or partially bonded to the skin-facing side of the chassis 11 by hot melt adhesive (not shown). The rear end of the liquid-absorbent structure 12 is sandwiched between the second inner sheet and the second outer sheet and thereby it is possible to prevent body waste from leaking from the rear end of the liquid-absorbent structure 12.

It should be appreciated that the first and second inner sheets 32, 33 are not limited to extend only in the front and rear waist region but may be arranged to extend further into the crotch region 15. Instead of placing the fixing sheet 45 on the skin-facing side, it is also possible to form the chassis 11 as a whole from the outer sheet and the inner sheet each having a shape corresponding to the outer shape of the diaper 10 and, if desired, to elasticize the diaper 10 as a whole.

It should be appreciated here that, while the following description will refer only to the first laminated sheet 37 in the front waist region 13, the description is true also with respect to the second laminated sheet 38 in the rear waist region 14.

As has previously been described, the first outer sheet 30 is subjected to thermocompression-bonding treatment from its outer surface toward its inner surface and is thereby formed on its whole area with a plurality of thermocompression-bonded spots (debossed spots) 20. In each of the debossed spots 20, the outer surface of the outer sheet 30 is thermocompression-bonded by, for example, an embossing roll and the crimped fibers 63 are compressed in the thickness direction of the outer sheet 30.

Figure 5:
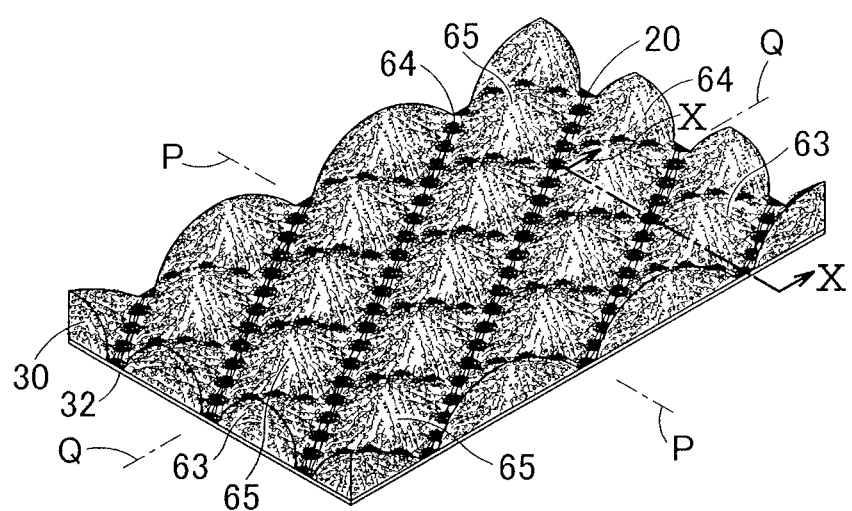
FIG. 5 is a partially scale-enlarged perspective view showing an outer surface of the diaper.

Referring to FIG. 5, many thermocompression-bonded spots 20 arranged intermittently in a given direction so as to form thermocompresssion bonding lines. In this way, two or more rows 21 of thermocompression-bonding lines extending at an angle of approximately 45° on one side with respect to the transverse axis Q and two or more columns 22 of thermocompression-bonding lines extending at an angle of approximately 45° on the opposite direction with respect to the transverse axis Q and intersecting with the rows 21 of thermocompression-bonding lines are formed.

Each pair of the rows 21 of thermocompression-bonding lines extend in parallel to each other and each pair of the columns 22 of thermocompression-bonding lines intersect with each other to define a plurality of substantially rhombic non-thermocompressed regions 64 each surrounding by these rows and columns 21, 22. In each of the non-thermocompressed regions 64, a group of the crimped fibers are concentrated under contraction of the first inner sheet 32 lying inside and, in consequence, the first outer sheet 30 is formed in its thickness direction with a plurality of protuberances to make the non-thermocompressed region 64 bulky. As shown by FIG. 1, the rows and columns 21, 22 of the thermocompression-bonding lines may be regularly shaped and arranged to form the outer surface of the diaper 10 with a quilt-like pattern.

The first outer sheet 30 is preferably formed of a thermal adhesive spun bonded non-woven fabric having a mass in a range of about 15 to 40 g/m$^2$, preferably in a range of about 25 to 35 g/m$^2$ and a fiber density in a range of about 0.1 to 0.06 g/cm$^3$, preferably in a range of about 0.07 to 0.09 g/cm$^3$. It is also possible to form the first outer sheet 30 of a plurality of layers so far as at least the outermost fiber layer comprises the crimped fibers 63. The fiber layer on the side of the first inner sheet 32 may comprise non-crimped fibers.

The first inner sheet 32 is preferably formed of a non-woven fabric of thermal adhesive elastomeric fiber having a mass in a range of about 20 to about 50 g/m$^2$, preferably in a range of about 30 to about 40 g/m$^2$ and a fiber density in a range of about 0.01 to about 0.04 g/cm$^3$, preferably in a range of about 0.025 to about 0.035 g/cm$^3$. More specifically, the first inner sheet 32 may be formed of mixed fibers of thermoplastic polyurethane polymer with a thermoplastic polymer other than thermoplastic polyurethane polymer such as styrene-based elastomer, polyolefin-based elastomer, vinyl chloride-based elastomer, amide-based elastomer, or polyolefin polymer such as polyethylene, polypropylene or polystyrene.

It is also possible to form the first inner sheet 32 of mixed fibers consisting of elastomeric fibers and non-elastomeric fibers. Use of such mixed fibers will make it possible to alleviate undesirable friction between elastomeric fibers and the wearer's skin. In other words, non-elastomeric fibers mixed in the first inner sheet 32 serve to improve slip properties of the first inner sheet 32 on the wearer's skin and thereby to improve flexibility as well as texture of the first inner sheet 32. In addition, mixing of non-elastomeric fibers makes it possible to adjust the stretch properties of the first inner sheet 32.

The first inner sheet 32 is bonded under tension at a stretch ratio of about 1.5 to 3.0 in the transverse direction to the first outer sheet 30 so that contraction of the first inner sheet 32 may enhance bulkiness of the crimped fiber layer constituting the first outer sheet 30.

Figure 6:
FIGS. 6(*a*) and 6(*b*) are diagrams illustrating patterns in which crimped fibers are crimped.
Figure 6:

Referring to FIG. 6(a) and FIG. 6(b), FIG. 6(a) illustrates two-dimensionally crimped fibers in wavy pattern and FIG. 6(b) illustrates three-dimensionally crimped fiber(s) in a coiled or spiral pattern. In the thermocompression-bonded spots, the individual component fibers are fusion-bonded one to another and, in the case of the crimped fiber(s) 63 obtained by the well known spun bonding method, melt-spun fibers of polymer as original material are dispersed to form a web. These fibers may at least partially be weakly fusion-bonded or interlaced in the non-thermocompressed regions also depending on types of treatments carried out in the course of forming the web. While such fusion-bonded or interlaced fibers in the non-thermocompressed regions may be partially released one from another by loading appropriate tension onto the fiber web as a material for the outer sheet 30 in the production process for the article. However, all the fibers forming the non-thermocompressed regions are preferably released one from another without being fusion-bonded or interlaced. In consideration of this, should all the fibers be fusion-bonded or interlaced together, a predetermined tension is loaded onto the fiber web and thereby the undesirable fusion-bonding or interlacing is completely eliminated according to the present invention.

The two dimensional crimp can be formed by, for example, a buckling method (indentation) or a known gear crimping method and relatively regularly crimped fibers are obtained by such method (See FIG. 6(a)). The three dimensional crimp can be formed by, for example, a false-twist crimping method or a scratch crimping method. The false-twist crimping method creates a relatively irregular crimp pattern and the scratch crimping method creates a relatively regular crimp pattern. To form the three dimensional crimp, a heat shrinkage crimping method is also available. When the heat shrinkage crimping method is employed, side-by-side type or core-in-sheath type conjugate fibers may be melt-spun from two or more types of polymer having different melting points, for example, polypropylene and polyethylene may be used as original materials to develop the desired crimp caused by the differential heat shrinkage derived from the differential melting point. Use of the eccentric core-in-sheath type conjugate fiber, of which the core is formed of polypropylene and the sheath is formed of ethylene/propylene copolymer, obtained by the heat shrinkage crimping method is preferable in view of various factors such as the number of crimps, the percentage of crimp, the crimp stretch rate, and the crimp recovery rate. The crimped fiber 63 illustrated by FIG. 6(b) is of the eccentric core-in-sheath type.

While a crimp percentage of the crimped fiber 63 may be appropriately regulated, in the case of filament fiber having fineness in a range of about 0.5 to about 3.0 deniers, depending on the desired flexibility of the first outer sheet 30 and the elongation, the fiber of which the number of crimps is in a range of about 10 to about 25/25 mm may be used as the fiber having relatively high percentage of crimp and the fiber of which the number of crimp is in a range of about 5 to about 10/25 mm may be used as the fiber having relatively low percentage of crimp.

Figure 7:
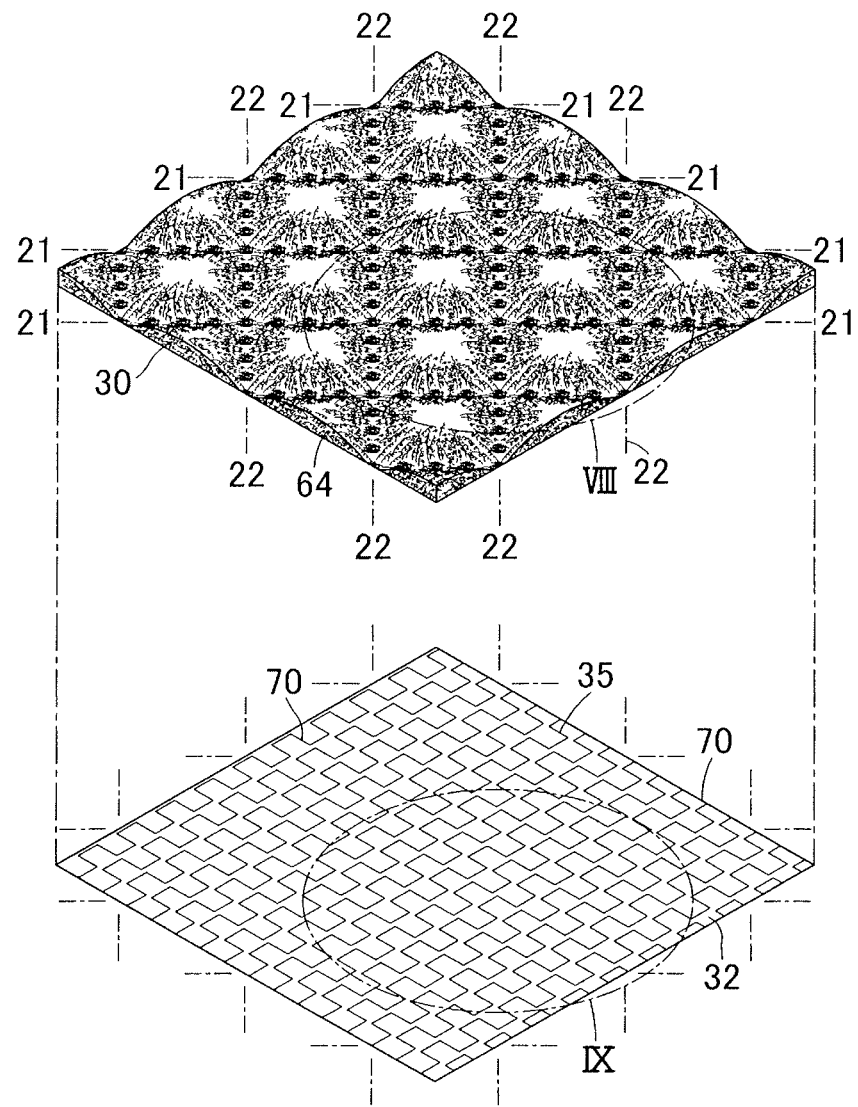
FIG. 7 is a diagram illustrating a first laminated sheet in a delaminated state.
Figure 8:
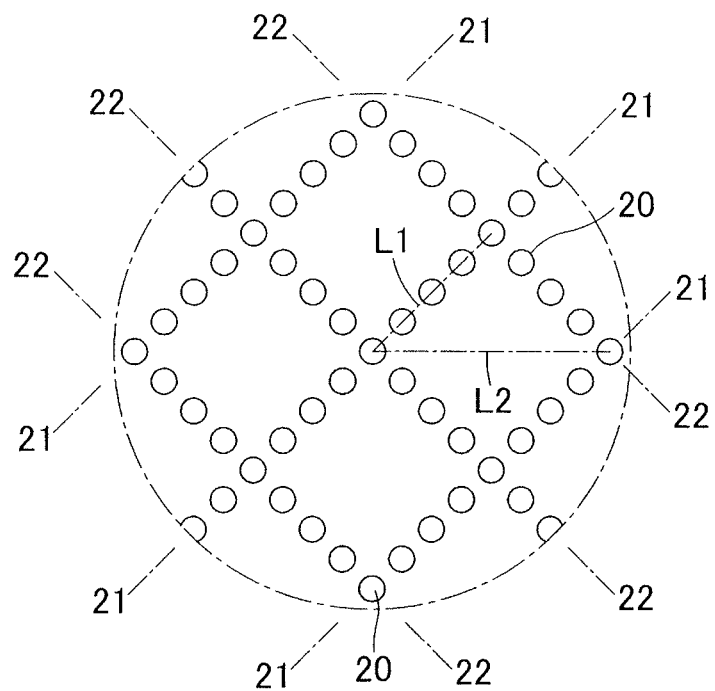
FIG. 8 is a partially scale-enlarged diagram illustrating thermocompression-bonding lines in a region encircled by the broken line VIII in FIG. 7.
Figure 9:
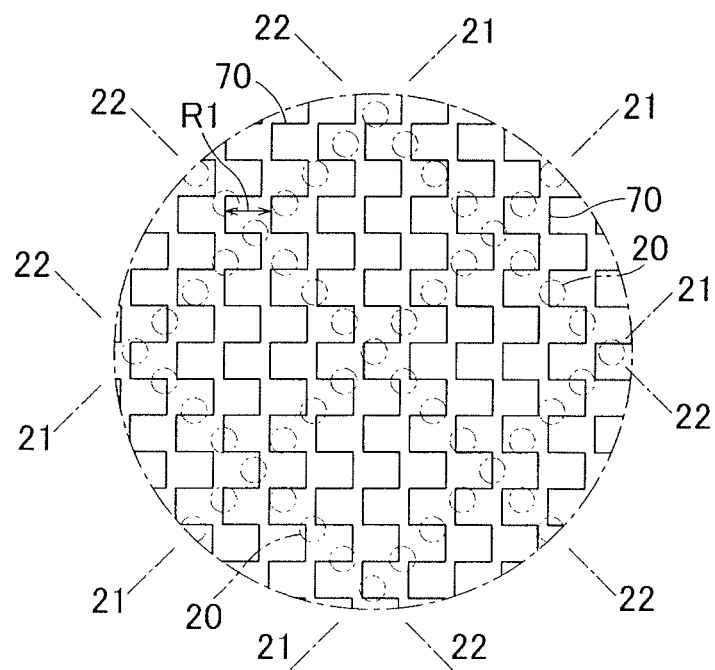
FIG. 9 is a partially scale-enlarged diagram illustrating a coating pattern of first adhesive in a region encircled by the broken line IX in FIG. 7.

Referring to FIGS. 7-9, in FIG. 7, the first inner sheet 32 is not bonded to the first outer sheet 30 and, in consequence, the non-thermocompressed regions 64 are still not formed with protuberances 65. In FIG. 9, the thermocompression-bonded spots (debossed spots) 20 forming the rows and columns 21, 22 of the thermocompression-bonded lines are indicated by broken lines.

In FIGS. 7 and 8, each of the thermocompression-bonded spots 20 forming the rows and columns 21, 22 of the thermocompression-bonding lines has a cross-sectional shape substantially in a circle having a diameter in range of about 0.4 to about 0.8 mm. The non-thermocompressed region 64 defined by the rows and columns 21, 22 of the thermocompression-bonding lines intersecting each other has a substantially rhombic shape, length L1 on a side may be in a range of about 7.0 to about 9.0 mm and length L2 on its diagonal may be in a range of about 6.0 to about 8.0 mm. It should be appreciated that respective sizes of the thermocompression-bonded spot 20 and the non-thermocompressed region 64 may be appropriately regulated and it is possible to provide the thermocompression-bonded spot 20 in various shapes of well known art other than rhombus, for example, in the shape of a rectangle, about 0.4 to about 0.7 mm on a side, or an ellipsoid or a triangle.

In FIGS. 7 and 9, the first adhesive 35 is hot melt adhesive applied at a mass in a range of about 1.0 to about 5.0 g/m² to define a plurality of bonding lines 70 extending in the longitudinal direction (i.e. parallel to the longitudinal axis) and spaced from one another in the transverse direction. Each bonding line substantially comprises an array having a shape of a series of "omega". Specifically, each bonding line comprises a continuous repeated pattern formed by alternating longitudinally and transversely extending line portions, wherein adjacent longitudinally extending line portions are spaced from one another in the transverse direction, and joined to one another, by a transverse extending line portion, and adjacent transversely extending line portions are spaced from one another in the longitudinal direction, and joined to one another, by a longitudinally extending line portion. All of the bonding lines are in register with one another, such that all of the line portions of each line portion lie parallel to corresponding line portions of all of the other line portions.

The pattern of the hot melt adhesive is not limited to the series of omega, as described above, but the hot melt adhesive may be applied in any other well known patterns such as a spiral-, dot-, wave- or grid-patterns.

While the hot melt adhesive is not limited to any particular type and well known types of hot melt adhesive may be selectively used, it is preferred to use rubber-based adhesive such as SBS (styrene-butadiene-styrene)-based hot melt adhesive or SIS (styrene-isoprene-styrene)-base adhesive from the viewpoint that the elasticity of the first inner sheet 32 should be is maintained as far as possible. Each of the bonding lines 70 has a line width preferably in a range of about 0.01 to about 0.1 mm, more preferably in a range of about 0.03 to about 0.07 mm and an area percentage versus the entire inner surface of the first inner sheet 32 is preferably in a range of about 2 to about 10%, more preferably in a range of about 4 to about 6%.

A distance R1 between each pair of the adjacent bonding lines 70 (measured by the transverse distance between corresponding longitudinally extending line portions of adjacent bonding lines, as shown in FIG. 9) is preferably in a range of about 1.0 to about 2.5 mm, more preferably in a range of about 1.5 to about 2.0 mm. Under these conditions, the bonding lines 70 may be formed of the first adhesive 35 to assure that the inner surface of the first inner sheet 32 is substantially over its entire area coated with hot melt adhesive in a substantially uniform pattern of two or more arrays of continuous "omega"s. In this way, the non-thermocompressed regions 64 in the outer surface of the first outer sheet 30 can be formed with the protuberances 65 distributed as evenly as possible. These protuberances 65 improve flexibility of the first laminated sheet 37 and create a quilt-like pattern providing a decorative outer appearance of the diaper.

Figure 10:
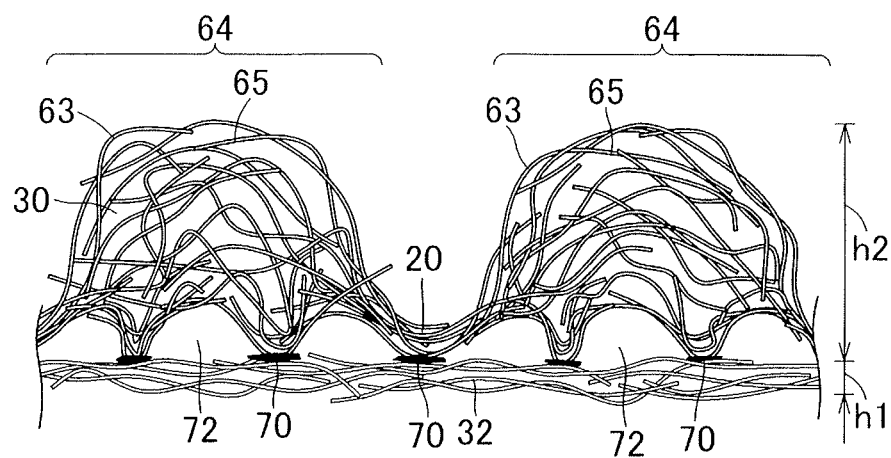
FIG. 10 is a partially scale-enlarged sectional view taken along the line X-X in FIG. 5.

As will be apparent from FIG. 10, after the first laminated sheet 37 has been formed by subjecting the first outer sheet 30 to thermocompression-bonding treatment so that the first outer sheet 30 and the first inner sheet 32 may be bonded to each other by the first adhesive 35, the crimped fibers 63 in the non-thermocompressed regions 64 each surrounded by the rows and columns 21, 22 of the thermocompression-bonding lines become bulky and the protuberances 65 are formed to extend convexly outward in the thickness direction of the outer sheet 30.

Specifically, on the assumption that the first inner sheet 32 has a height dimension h1 in a range of about 0.5 to about 1.0 mm, the protuberances 65 of the first outer sheet 30 have a height dimension (measured from the inner sheet 32 to tops of the respective protuberances 65) in a range of about 2.0 to about 3.0 mm.

Now it will be described hereunder how and why the non-thermocompressed regions 64 of the first outer sheet 30 become bulky. At least the outermost fiber layer of the first outer sheet 30 is defined by the crimped fibers 63 which have been fusion-bonded together in the respective thermocompression-bonded spots 20 formed by the thermocompression-bonding treatment. In the regions of the first outer sheet 30 except these thermocompression-bonded spots 20, i.e., in the non-thermocompressed regions 64 surrounded by the bonding lines formed of the thermocompression-bonded spots 20, at least a part of the crimped fibers 63 is left free one from another and freely movable. So far as at least a part, preferably all or substantially all of the crimped fibers 63 in the non-thermocompressed regions 63 can be left free one from another, it is assured that the texture of the diaper 10 on its outer surface can be improved.

The inner surface of the first outer sheet 30 is bonded to the first inner sheet 32 having stretch properties or elastic stretch properties higher than that of the first outer sheet 30 by the first adhesive 35 so that the crimped fibers 63 in the non-thermocompressed regions may follow the movement of the first inner sheet 32. In consequence, upon contraction of the first inner sheet 32, the distance between each pair of the adjacent bonding lines 70 is reduced in comparison to the corresponding distance when the first inner sheet 32 is under tension and the crimped fibers 63 protrude outward in the thickness direction of the first outer sheet 30 to form voids 72 in the non-bonded regions defined between the bonding regions. In this way, the first laminated sheet 37 as a whole provides "an airy and flexible texture".

More specifically, the first outer sheet 30 preferably exhibits a cantilever stiffness (JIS L1096) in a range of about 45.0 to about 65.0 mm as the inner sheet 32 contracts and, in this state, a KES compression value of the first laminated sheet 37 as a whole is in a range of about 0.2 to about 0.3 gf cm/cm². The first laminated sheet 37 of the present invention has flexibility higher than that of a laminated sheet consisting of two fibrous non-woven fabric layers, which has conventionally been used as the outer sheet of disposable diaper. Consequentially, the first laminated sheet 37 is capable of achieving "an airy and flexible texture" experienced by the wearer and the helper.

<Total Luminous Transmittance>

TABLE 1 set up below comparatively indicates the total luminous transmittance measured on the first laminated sheet 37 of the invention comprising the inner sheet 32 and the first outer sheet 30 bonded to each other by adhesive 35 and a laminated sheet comprising an elastic sheet and an inelastic sheet which has conventionally been used as an outer sheet of disposable diaper.

<Samples for Measurement>

An elastic fibrous non-woven fabric having a mass of 30 g/m² was used as the first inner sheet 32, a spun bonded fibrous non-woven fabric comprising crimped fibers and having a mass of 30 g/m² was used as the first outer sheet 30 and the inner surface of the first inner sheet 32 was coated with hot melt adhesive having a mass of 2 g/m² in the pattern of continuous "omega"s. With the first inner sheet 32 stretched in the transverse direction at the stretch ratio of 2.4, these two sheets were bonded together to form the first laminated sheet 37. As a conventional laminated sheet, an elastic fibrous non-woven fabric having a mass of 30 g/m² was bonded to a spun bonded non-woven fabric of non-crimped fibers by the hot melt adhesive having the same mass as the above-mentioned hot melt adhesive to form the laminated sheet.

<Method of Measurement>

Total luminous transmittance was measured in accordance with JIS-K7105 and, for this measurement, a color-difference meter (color difference meter of flicker photometer type Z-300A manufactured by NIPPON DENSHOKU INDUSTRIES Co., Ltd.) was used. Specifically, samples each having a size of 50 mm in width and 40 mm in length were obtained and clamped in a turbidimeter to determine TT values as the total luminous transmittances (%) of the respective samples. The measurement was carried out ten (10) times for the conventional spun bonded non-woven fabric of non-crimped fibers, the outer sheet according to the present invention, the conventional laminated sheet and the first laminated sheet 37 according to the present invention, respectively, and respective average values were calculated.

<Result of Measurement>

As will be apparent from the measurement result indicated by TABLE 1 set up above, there was no significant difference between the conventional spun bonded non-woven fabric of non-crimped fibers and the outer sheet 30 according to the present invention so far as the total luminous transmittance is concerned. However, after the conventional spun bonded non-woven fabric and the outer sheet 30 according to the present invention had been bonded to the elastic sheet and the inner sheet 32, respectively, the conventional laminated sheet exhibited total luminous transmittance of about 49% and the first laminated sheet 37 according to the present invention exhibited total luminous transmittance of 40% or lower. As will be appreciated from such specific measurement values, total luminous transmittance of the first laminated sheet 37 is lower than that of the conventional laminated sheet. This is for the reason that the crimped fibers become further bulky in the thickness direction of the outer sheet 30 and luminous transmittance of the first laminated sheet 37 as a whole is remarkably lowered as the outer sheet 30 is bonded to the inner sheet 32 by the first adhesive 35.

As has been described above, the first laminated sheet 37 consisting of the first inner sheet 32 and the first outer sheet 30 has the luminous transmittance noticeably lowered as these two sheets 32, 30 are bonded to each other. Consequentially, the regions of the first laminated sheet 37 in the front and rear waist regions 13, 14 take on faded white as a whole (assumed

TABLE 1

| | Total Luminous Transmittance (%) | | | |
|---|---|---|---|---|
| | Non-crimped spun bonded non-woven fabric | Spun bonded non-woven fabric of crimped fiber (outer sheet) | Conventional laminated sheet (elastic non-woven fabric + non-woven fabric of non-crimped fiber) | First laminated sheet according to the invention (inner sheet + outer sheet) |
| 1 | 66.82 | 74.10 | 50.10 | 38.81 |
| 2 | 70.58 | 72.19 | 48.89 | 45.02 |
| 3 | 73.51 | 71.05 | 47.56 | 34.91 |
| 4 | 78.94 | 75.90 | 46.99 | 38.67 |
| 5 | 73.68 | 71.64 | 51.66 | 41.21 |
| 6 | 68.17 | 72.84 | 53.82 | 39.22 |
| 7 | 75.12 | 77.72 | 48.97 | 39.62 |
| 8 | 72.01 | 72.07 | 46.29 | 41.16 |
| 9 | 69.98 | 69.10 | 53.90 | 41.00 |
| 10 | 72.84 | 73.40 | 45.69 | 37.90 |
| av. | 72.17 | 73.00 | 49.39 | 39.75 | that all the sheet materials are white) and there is no possibility that the wearer's skin might be visually recognized through these regions. Between the region formed of the first laminated sheet 37 and the region occupied by the liquid-absorbent core assembly 55, there is substantially no difference in total luminous transmittance and the diaper 10 as a whole has the outer appearance like cotton underwear.

<Second Embodiment>

Figure 11:
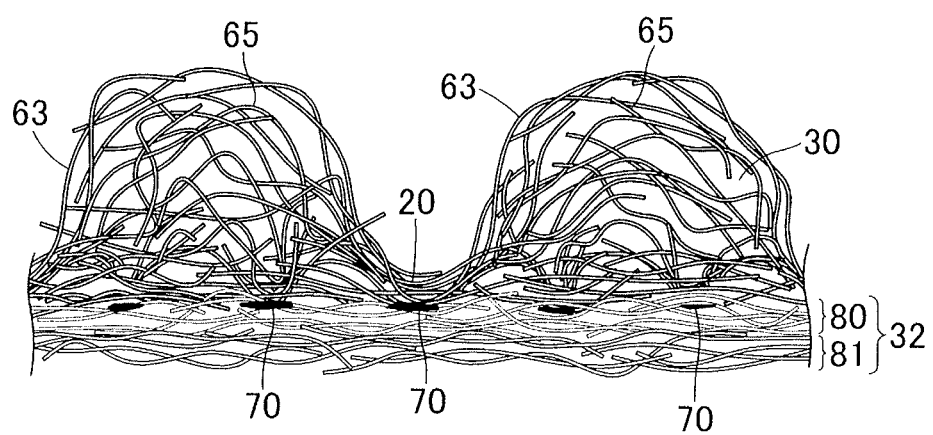
FIG. 11 is a partially scale-enlarged sectional view similar to FIG. 10 taken along the corresponding line in the diaper according to a second embodiment of the present invention.

Referring to FIG. 11, the basic aspect of the diaper 10 according to this embodiment is similar to the diaper 10 according to the first embodiment and the following description will be limited to the aspect differing from the first embodiment.

According to the present embodiment, the first inner sheet 32 comprises an outer layer 80 lying adjacent to the first outer sheet 30 and an inner layer 81 lying adjacent to a lower surface of the outer layer 80. The outer layer 80 is formed of blend fibers comprising elastomeric fibers such as polyurethane and non-elastomeric fibers such as polypropylene and, in contrast to the outer layer 80, the inner layer 81 is formed of elastomeric fibers only. Content percentage of non-elastomeric fibers in the blend fibers of the outer layer 80 may be in a range of about 50% to 65% by mass, preferably in a range of about 55 to about 60% by mass to improve the texture.

The outer layer 80 is formed of blend fibers of non-elastomeric fibers and a surface of the outer layer 80 to be put flat together with and to be bonded to the outer sheet 30 is more flat than the case in which the outer layer 80 is formed of elastomeric fibers only. This means that the surface area over which the outer layer 80 is to be bonded to the crimped fibers 63 constituting the first outer sheet 30 is advantageously enlarged and the first inner sheet 32 can be stably bonded to the first outer sheet 30. In addition, when the fiber layer constituting the first outer sheet 30 to be bonded to the outer layer 80 is formed of non-crimped fibers, it is assured that the surface over which the outer layer 80 to be bonded to the first outer sheet 80 is further more flat and the first inner sheet 32 can be more stably bonded to the first outer sheet 30.

The first outer sheet 30, the outer layer 80 and the inner layer 81 of the first inner sheet 32 preferably respectively have elongation percentages as follows: the first outer sheet 30 has elongation percentage in a range of about 60 to about 80% in the longitudinal direction and in a range of about 200 to about 250% in the transverse direction; the outer layer 80 has elongation percentage in a range of about 100 to about 120% in the longitudinal direction and in a range of about 200 to about 250% in the transverse direction; and the inner layer 81 has elongation percentage in a range of about 180 to about 200% in the longitudinal direction and in a range of about 250 to about 300% in the transverse direction.

Elongation percentages of these sheets (fibrous layers) 30, 32, 80, 81 indicate a correlation such that the elongation percentage of the outer layer 80 is higher than the elongation percentage of the first outer sheet 30 and the elongation percentage of the inner layer 81 is higher than that of the outer layer 80. In other words, the outer layer 80 having a relatively low elongation percentage may be bonded to the first outer sheet 30 to assure that the first outer sheet 30 more easily follows movement of the first inner sheet 32 than the case in which the inner layer 81 having a relatively high elongation percentage is directly bonded to the outer sheet 30. In this way, the outer sheet 30 can be prevented from being delaminated from the inner sheet 32.

<Third Embodiment>

Figure 12:
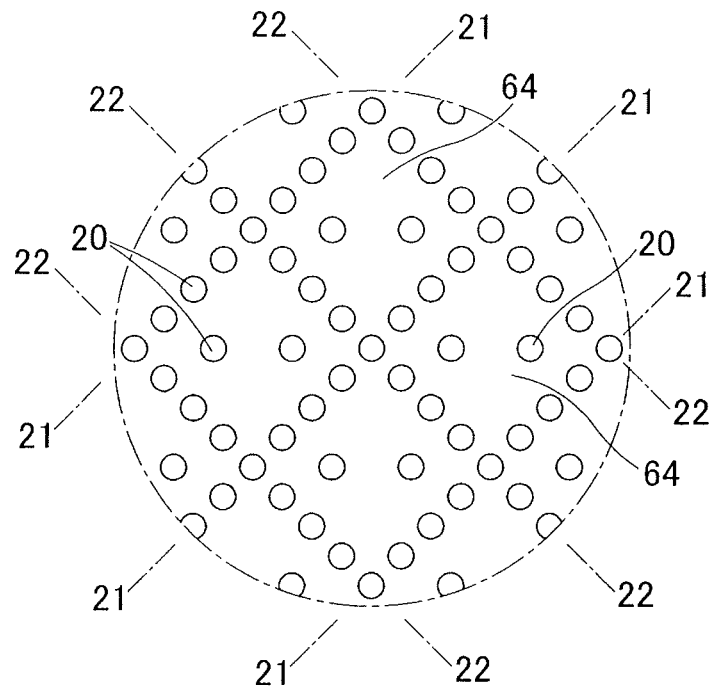
FIG. 12 is a partially scale-enlarged diagram similar to FIG. 9 illustrating thermocompression-bonding lines in the diaper according to a third embodiment of the present invention.

Referring to FIG. 12, the basic aspect of the diaper 10 according to this embodiment is similar to the diaper 10 according to the first embodiment and the following description will be limited to the aspect differing from the first embodiment.

According to the present embodiment, in addition to the thermocompression-bonded spots 20 forming the rows and columns 21, 22 of the thermocompression-bonding lines, two or more thermocompression-bonded spots 20 are formed in the central zone of each non-thermocompressed region 64 (FIG. 12). These two or more additional thermocompression-bonded spots 20 create relatively small protuberances 65 in the central zone of the non-thermocompressed region 64 and thereby flexibility of the first laminated sheet 37 as a whole is improved in comparison to the first embodiment.

<Fourth Embodiment>

Figure 13:
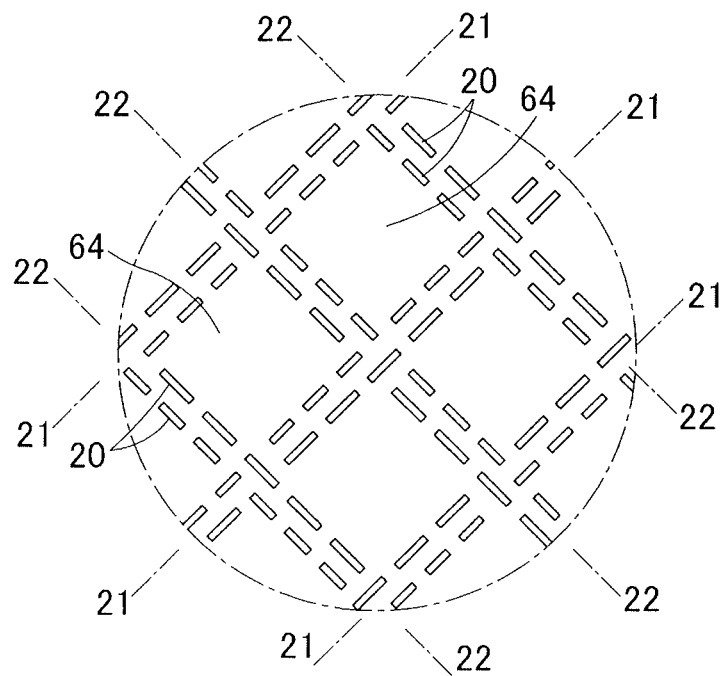
FIG. 13 is a partially scale-enlarged diagram similar to FIG. 8 illustrating thermocompression-bonding lines in the diaper according to a fourth embodiment of the present invention.

Referring to FIG. 13, the basic aspect of the diaper 10 according to this embodiment is similar to the diaper 10 according to the first embodiment and the following description will be limited to the aspect differing from the first embodiment.

According to the present embodiment, the rows and columns 21, 22 of the thermocompression-bonding lines are formed by alternating small and large rectangular thermocompression-bonded spots 20 in staggered pattern. With such arrangement, a total area of the non-thermocompression-bonded regions 64 is smaller than in the case of the first embodiment. Consequentially, the area ratio of the non-thermocompressed regions 64 versus the first outer sheet 30 as a whole is lowered and the area ratio of the thermocompression-bonded spots 20 versus the first outer sheet 30 as a whole is raised. The present embodiment is particularly effective to restrict fluffing of the first outer sheet 30 as a whole and the crimped fibers 63 of the first outer sheet 30 can be restricted from becoming excessively bulky (becoming excessively fluffy) due to contraction of the first inner sheet 32.

<Mechanical Properties of First and Second Laminated Sheets 37, 38>

Table 2 shows mechanical properties such as a tensile property, a bending property, a surface property, a shearing property and a compression property of first and second laminated sheets 37, 38 according to one or more embodiments of the present invention measured by the KES method and compared with those of corresponding members of other known diapers.

TABLE 2

| Property | Characteristic Values (Unit) | Front waist region | | | Rear waist region | | |
| --- | --- | --- | --- | --- | --- | --- | --- |
| | | Example 1 | Comparative Example 1 | Comparative Example 2 | Example 1 | Comparative Example 1 | Comparative Example 2 |
| Tensile | EMT (%) | 115.1 | 120.2 | 160.4 | 98.2 | 120.7 | 119.4 |
| | LT (—) | 0.616 | 0.731 | 0.683 | 0.680 | 0.532 | 0.451 |
| | WT (gf/cm$^2$) | 35.47 | 44.07 | 54.80 | 33.17 | 32.27 | 26.97 |
| | RT (%) | 42.1 | 53.0 | 59.6 | 42.8 | 54.4 | 59.5 |

TABLE 2-continued

|  |  | Front waist region | | | Rear waist region | | |
| --- | --- | --- | --- | --- | --- | --- | --- |
| Property | Characteristic Values (Unit) | Example 1 | Comparative Example 1 | Comparative Example 2 | Example 1 | Comparative Example 1 | Comparative Example 2 |
| Bending | B (gf * cm$^2$/cm) | 0.1054 | 0.1454 | 0.2431 | 0.1436 | 0.1659 | 0.2440 |
|  | 2HB (gf * cm$^2$/cm$^2$) | 0.1379 | 0.2450 | 0.2994 | 0.1598 | 0.2608 | 0.3144 |
|  | Bwale (gf * cm$^2$/cm) | 0.2421 | 0.8472 | 1.1094 | 0.2167 | 0.3094 | 1.6495 |
| Shearing | G (gf/cm * deg) | 0.450 | 0.587 | 0.800 | 0.443 | 0.553 | 0.693 |
|  | 2HG (gf/cm) | 1.033 | 1.350 | 1.950 | 1.050 | 1.333 | 1.433 |
|  | 2HG5 (gf/cm) | 1.000 | 1.333 | 1.767 | 1.033 | 1.300 | 1.383 |
| Compression | LC (—) | 0.864 | 0.887 | 0.594 | 0.806 | 0.856 | 0.623 |
|  | WC (gf * cm/cm$^2$) | 0.503 | 0.284 | 0.294 | 0.310 | 0.539 | 0.559 |
|  | RC (%) | 39.2 | 40.2 | 42.3 | 37.2 | 36.9 | 53.9 |
| Surface | MIU (—) | 0.447 | 0.628 | 0.549 | 0.420 | 0.623 | 0.559 |
|  | MMD (—) | 0.0106 | 0.0182 | 0.0147 | 0.0114 | 0.0156 | 0.0132 |
|  | SMD (μm) | 3.20 | 7.98 | 5.83 | 2.37 | 5.98 | 6.81 |
| Thickness | T0 (mm) | 3.774 | 2.706 | 2.877 | 2.510 | 3.747 | 4.034 |

<Samples for Measurement>

The measurement was carried out 3 times for each of Example 1, Comparative Example 1 and Comparative Example 2 and respective average values were calculated. The disposable diaper 10 of large size according to one or more embodiments of the present invention is used as a sample for Example 1, the disposable diaper (A) of large size (which is marketed by Uni Charm Corp. as trade name "MOONYMAN") is used as a sample for Comparative Example 1 and the disposable diaper (B) of large size (which is marketed by another company) is used as a sample for Comparative Example 2. All of the diapers used as Example 1, Comparative Example 1 and Comparative Example 2 are so-called pant-type diapers and each of these diapers has an absorbent structure independently provided on the outermost sheet thereof. Each property, other than tensile property and shearing property, is measured for each of the front or rear waist region at the predetermined region thereof provided between one of the side edges and the absorbent structure. Each of tensile property and shearing property is measured for each of the front or rear waist region in which the absorbent article has been removed and side edges of the outermost sheet has been peeled off. Additionally, tensile property and shearing property are measured for each of the diapers with waist elastics and leg elastics present and the other properties are measured for each of the diapers with waist elastics and leg elastics removed.

EXAMPLES

The first laminated sheet 37 of the diaper 10 used as Example 1 comprises an elastic fibrous non-woven fabric having a mass of 30 g/m$^2$ used as the first inner sheet 32 and a spun bonded fibrous non-woven fabric comprising crimped fibers and having a mass of 30 g/m$^2$ used as the first outer sheet 30 wherein the inner surface of the first inner sheet 32 was coated with hot melt adhesive having a mass of 2 g/m$^2$ in the pattern of continuous "omega"s and these two sheets have been bonded together to form the first laminated sheet 37 with the first inner sheet 32 stretched in the transverse direction at the stretch ratio of 2.48. On the other hand, second laminated sheet 38 of the diaper 10 comprises an elastic fibrous non-woven fabric having a mass of 30 g/m$^2$ used as the second inner sheet 33 and a spun bonded fibrous non-woven fabric comprising crimped fibers and having a mass of 30 g/m$^2$ used as the second outer sheet 31 wherein the inner surface of the second inner sheet 33 was coated with hot melt adhesive having a mass of 2 g/m$^2$ in the pattern of continuous "omega"s and these two sheets have been bonded together to form the second laminated sheet 38 with the second inner sheet 33 stretched in the transverse direction at the stretch ratio of 2.48. The number of crimps of the crimped fibers of the first and second outer sheet 30, 31 is 15-20 times/25 mm.

Comparative Example 1

The diaper used as Comparative Example 1 has an outermost sheet (a laminated sheet) defining a whole contour of the diaper which comprises an inner sheet of a SMS fibrous non-woven fabric having a mass of 15 g/m$^2$ lying on a skin-facing side thereof and an outer sheet of a spun bonded fibrous non-woven fabric having a mass of 17 g/m$^2$ lying on a non-skin-faCing side thereof. Additionally, a plurality of waist elastic strands is provided between the inner sheet and the outer sheet on the whole area of the front and rear waist regions and attached by hot melt adhesive with the waist elastic strands stretched in the transverse direction at a stretch ratio of 2.9-3.4. Furthermore, a stretch ratio of each of the waist elastic strands depends on the region in which the respective waist elastic strand is provided.

Comparative Example 2

The diaper used as Comparative Example 2 has an outermost sheet (a laminated sheet) defining a whole contour of the diaper which comprises an inner sheet of a spun bonded fibrous non-woven fabric having a mass of 18 g/m$^2$ lying on a skin-facing side thereof and an outer sheet of an air-through fibrous non-woven fabric having a mass of 18 g/m$^2$ lying on a non-skin-facing side thereof. Additionally, a plurality of waist elastic strands is provided between the inner sheet and the outer sheet on the whole area of the front and rear waist regions and attached by hot melt adhesive with the waist elastic strands stretched in the transverse direction at the stretch ratio of 2.5-3.9. Furthermore, a stretch ratio of each of the waist elastic strands depends on the region in which the respective waist elastic strand is provided.

<Method of Measurement>

The KES method used for this measurement is described in the text book entitled "The Standardization and Analysis of Hand Evaluation (2nd. Edition)", published by the Textile Machinery Society of Japan, Jul. 10, 1980. Also, this method is described in WO 98/20822. Here, we basically refer to this text book for the measurement method and only conditions of measurement for each mechanical property are described herein below.

<Tensile Property>

Each sample of laminated sheet which has a width of 10 cm and an initial length of 2.5 cm is subjected to applied unidirectional extension stress up to 100 gf/cm and then tensile properties are measured using KES-FB1 manufactured by Katotech co. LTD with the speed of the deformation set at 0.4%/sec. From the tensile property curve obtained from the above measurement, several values are calculated: EMT—tensile extension percentage (%), LT—linearity of tensile property curve, WT—tensile work load (gf/cm$^2$) and RT—tensile restore percentage (%). Tensile property is measured only in the transverse direction since the usual diapers are extended only in the transverse direction.

<Bending Property>

Each sample having a width of 5 cm is fixed between chucks of KES-FB2 manufactured by Katotech co. LTD separated by 1 cm from one another and bent towards the inner surface by a maximum curvature of +2.5 cm$^{-1}$ and then bent towards the outer surface by a maximum curvature of −2.5 cm$^{-1}$ and finally allowed to return to its initial state for measurement of bending property thereof. The measurement is taken with the samples vertically suspended. Bending stiffness B which is a mean value of values for the longitudinal direction and for the transverse direction (gf*cm$^2$/cm) is calculated from the slope of bending moment vs. curvature, at a point at which it has become stable after the beginning of bending towards the inner surface; and the bending restore property 2HB (gf*cm$^2$/cm$^2$) is calculated from its hysteresis width. In addition, bending stiffness Bwale was also calculated and compared for the longitudinal direction only.

<Shearing Property>

Each sample having a width of 5 cm is clamped using KES-FB1 manufactured by Katotech co. LTD and shearing stiffness G (gf/cm*deg), in the transverse direction, unidirectional shearing hysteresis, at a shearing angle of 0.5 degrees 2HG (gf/cm), and unidirectional shearing hysteresis, at a shearing angle of 5 degrees 2HG5 (gf/cm), are measured under a force of 10 gf/cm. Shearing property is measured only in the transverse direction since the usual diapers are extended only in the transverse direction.

<Compression Property>

Each sample is extended by 1.2 times in the transverse direction and a predetermined area is compressed between steel boards each having a flat circular terminal of 20 mm$^2$ using KES-FB3 manufactured by Katotech co. LTD and then the compression property is measured at compression speed of 150 sec/mm and under a maximum compression of 10 gf/cm$^3$. The returning process is also measured at a predetermined speed. A linearity of compression property curve was obtained and compression work load WC (gf*cm/cm$^2$) and compression restore percentage RC (%) was calculated.

<Surface Property>

Each 10 cm×20 cm sample is settled on a smooth metal surface of the test table of KES-FB4 manufactured by Katotech co. LTD and, for measurement of roughness of surface, is contacted with a contactor having a width of 0.5 cm covered with a piano steel wire having a diameter of 0.5 mm, and, for measurement of surface friction, is contacted with 10 pieces of the same wire arranged on the sample and applied with a compressional force of 50 fg by dead weight. In the measurement of roughness of surface and surface friction, the samples were subjected to 20 gf/cm of uniaxial tensile force and moved at a determined speed of 0.1 cm/sec by 2 cm. From the result, mean friction coefficient MIU, standard deviation of friction coefficient MMD (only in the transverse direction) and mean deviation of roughness of surface SMD (micrometer) are calculated. In this measurement, only the inner surfaces were measured since the inner surface contact the wearer's skin directly.

<Thickness>

The thickness of each sample was measured under a pressure of 0.5 fg/cm$^2$ as per the KES-F standard measurement condition.

<Result of Measurement>

As shown in Table 2, among 17 parameters about basic texture values, for parameters of shearing property (G, 2HG, 2HG5), bending property (B, 2HB), surface property (MIU, MMD, SMD), compression work load WC and tensile restore percentage are better for Example 1 than those of Comparative Examples 1 and 2.

Specifically, for shearing property, while the larger value of each parameter means the higher stiffness and lower elasticity of the laminated sheet, shearing stiffness and shearing hysteresis 2HG, 2HG5 of the laminated sheet of the diaper of the Example 1 are smaller than those of the comparative examples 1 and 2. Consequently, the laminated sheet of the Example 1 is softer than those of the Comparative examples 1 and 2.

For bending property, while the larger value of each parameter means a higher difficulty of bending and restore from a bending position of the laminated sheet, bending stiffness B and bending hysteresis 2HB of the laminated sheet of the diaper of the Example 1 are smaller than those of the comparative examples 1 and 2. Consequently, the laminated sheet of the Example 1 is more flexible, easier to bend and more repellent than those of the Comparative example 1 and 2.

For surface property, while the larger value of each parameter means the higher friction property and the more roughness and the more uneven of the surface of the laminated sheet, mean friction coefficient MIU, standard deviation of friction coefficient MMD and mean deviation of roughness of surface SMD of the laminated sheet of the diaper of the Example 1 are smaller than those of the comparative example 1 and 2. Consequently, the laminated sheet of the Example 1 has a smoother inner surface (skin-contact surface) and a better texture than those of Comparative Examples 1 and 2.

Figure 15:
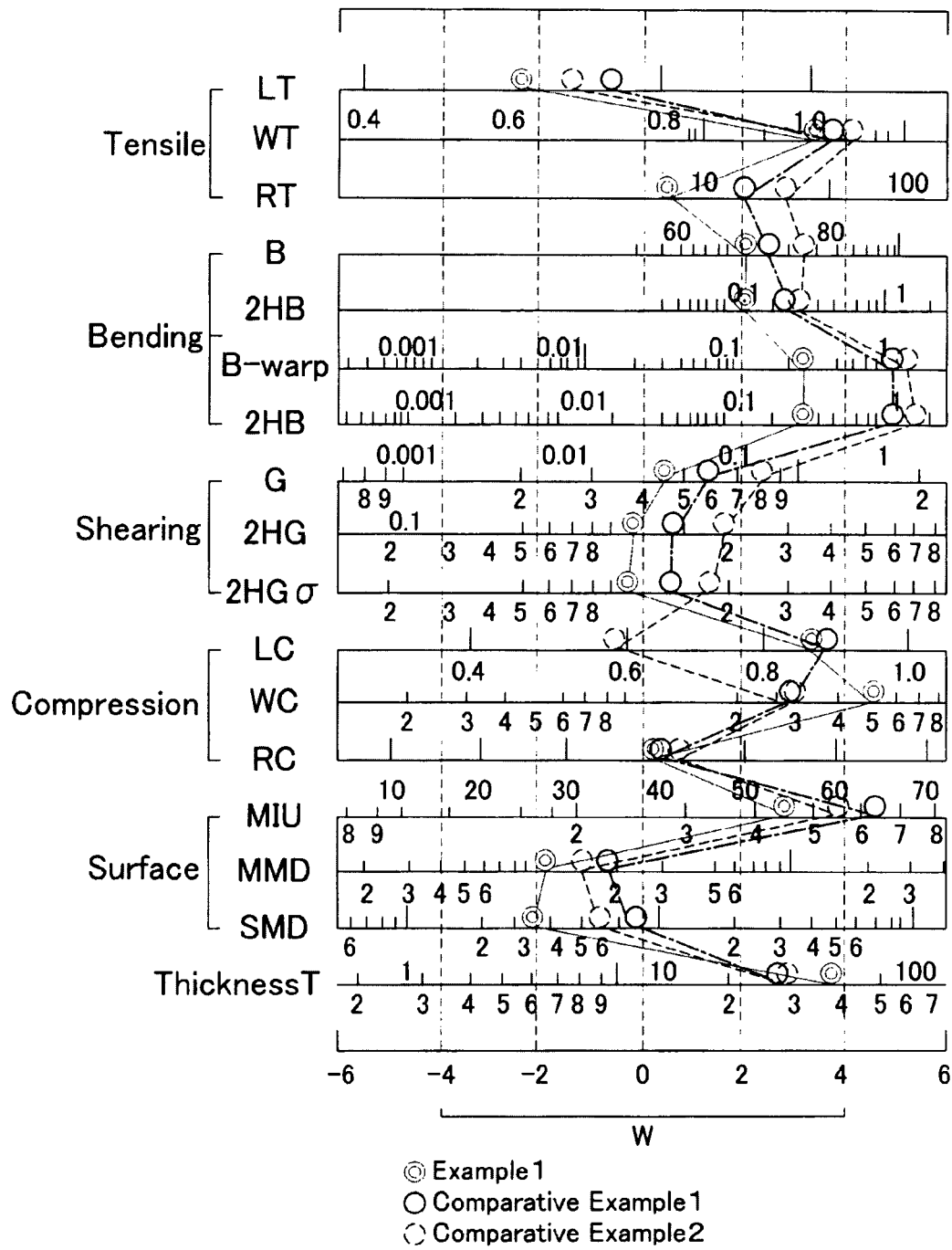
FIG. 15 is a table that shows the distribution of log values calculated from logarithmic transformation of the value of each parameter obtained by the measurement (except for mass).

FIG. 15 shows the distribution of log value calculated from logarithmic transformation of the value of each parameter obtained by the measurement (except for mass). FIG.15 shows that characteristic values are distributed almost symmetrically around average values. The inventors of the present application arrived at the newly formed conclusion that on this distribution, from −4.0 to +4.0 is the applicable range for preferable cotton garments. As described in the report entitled "A Development in the Objective Measurement of the Quality of Knitted Fabrics Used for Underwear", Sen'i Kikai Gakkaishi (Journal of the Textile Machinery Society of Japan) Vol. 39, No. 3, p. T33-T50, published by the Textile Machinery Society of Japan, 1986, the basic texture of a desired garment for winter, having such values, has an excellent hand value of Koshi (softness, flexibility), an excellent hand value of Numeri (smoothness) and an excellent hand value of Fukurami (balkiness). As shown in FIG. 15, the diaper of Example 1 has almost all characteristic properties included in this range W and therefore it has a garment-like basic texture. On the other hand, the diapers of Comparative examples 1 and 2 have values far from this range therefore do not have a garment-like hand value of Koshi (softness, flexibility).

Hand values of Koshi, Numeri and Fukurami can be calculated from characteristic values of the 16 parameters using the formula below:

$$HV = C_o + \sum_{i=1}^{16} C_i \frac{X_i - \overline{X}_i}{\sigma_i} \qquad \text{[Math. 1]}$$

HV; a hand value of basic texture
$X_i$; mechanical value of No. i
$\overline{X}$; mean value of $X_i$
$\sigma_i$; standard deviation of $X_i$
$C_0$, $C_i$; constant
i=1-16

Figure 14:
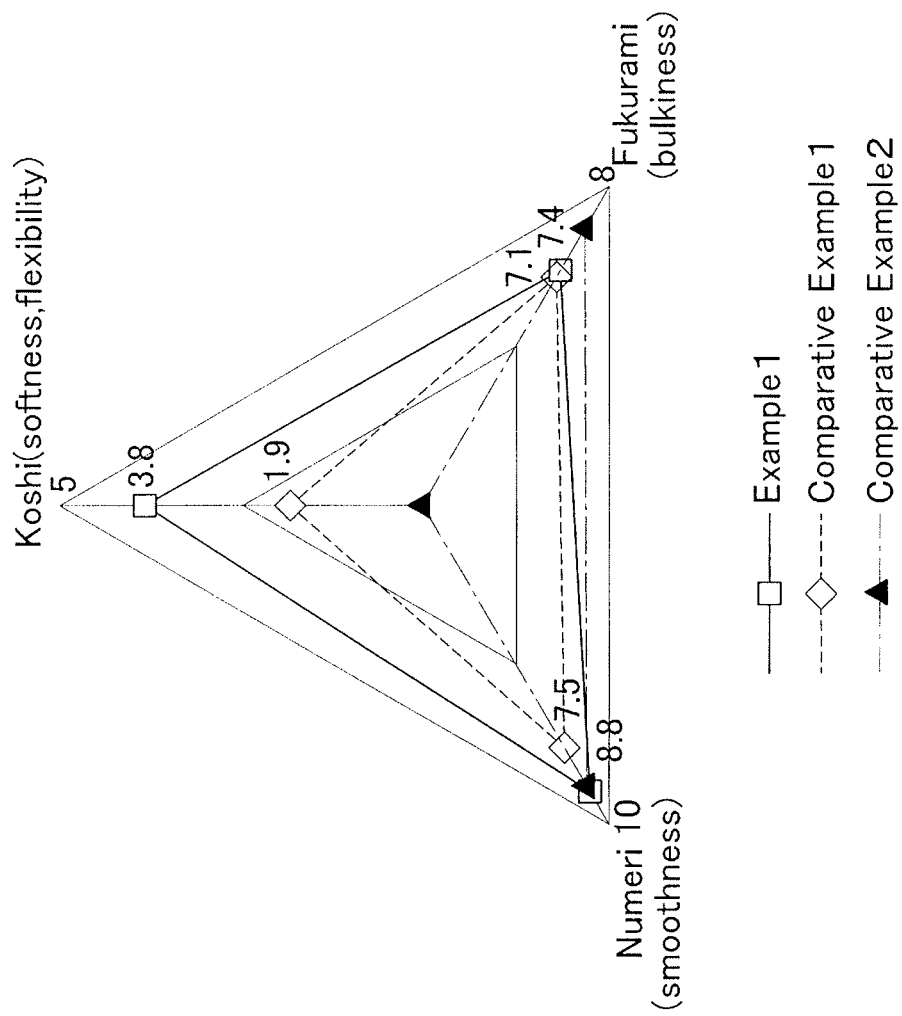
FIG. 14 is a chart showing the comparison between a basic texture of Example 1, Comparative Example 1 and 2.

FIG. 14 is a chart of values calculated from full-count value (10) subtructed hand values of Koshi, Numeri, Fukurami. As shown in FIG. 14, For Numeri and Fukurami, there is no big difference between values of Example and Comparative Examples, but for Koshi, the value of Example 1 is 3.8 while that of Comparative Example is 1.9, about a half value of that of Example 1.

The texture of the diaper cannot absolutely valued based on only KES value which is objective value to evaluate woven-fabric garments, but at least according to these data, the diaper of Example 1 has better Koshi, flexibility and so-called "flex and soft texture" than that of Comparative Example 1 (product of Uni charm).

Additionally, there is another examination data based on a monitoring test. Specifically, Example 1 and Comparative Example 1 are put on infants (29 subject babies) and amylase activity of each baby was measured for 3 minutes using "salivary amylase monitor" manufactured by Nipro corporation. Similar data for naked babies were obtained and difference between this data and the above data were calculated. As a result, an amount of amylase secreted by each baby put on the diaper of Example 1 was apt to be smaller than that of Comparative Example 1.

According to the knowledge of the inventor of the present application, the larger amount of secreted salivary amylase means the more stress is felt by babies. Consequently, infants put on the diaper of Example 1 is more relaxed than those put on the Comparative Example 1.

This result means that stress experienced by the wearer because of clamp of elastic strands at the waist or leg-surroundings, roughness of the surface of the diaper and stuffy condition inside the diaper and the like is reduced with the diaper of Example 1. Specifically, since elastic tapes are used at leg-surroundings and laminated sheets comprising an elastic sheet as an inner sheet and an outer sheet including crimped fibers are used for front and waist regions, the diaper of Example 1 does not locally clamp the wearer's waist or leg region and fits on a side region of skin of the wearer. Furthermore, as shown in characteristic values of the surface of Example 1 as measured above, the outer sheet has a smooth and soft surface having a quilt-like texture to reduce stress for wearing the diaper.

Materials for the respective members constituting the diaper 10 are not limited to those described in this specification and various types of material conventionally used in the relevant technical field may be selectively used. Furthermore, the diaper 10 is not limited to a pant-type disposable diaper and the present invention is applicable also to so-called open-type diapers having front and rear waist regions not previously bonded together along side edges of the respective waist regions or to diapers having the front waist region 13, the rear waist region 14 and the crotch region 15 continuously formed.

So far as the first and second outer sheets 30, 31 as well as the inner sheets 32, 33 are concerned, these components of the disposable wearing article according to the present invention may be effectively used for various bodily fluid-absorbent wearing articles such as urine-absorbent pads and menstruation napkins.

The aspects of the present invention described above may be arranged in at least the following item(s):

(i) A disposable wearing article (10) having a longitudinal axis (P) extending in a longitudinal direction, a transverse axis (Q) orthogonal to the longitudinal axis and extending in a transverse direction, and comprising a skin-facing side, a non-skin-facing side, a first waist region (13) corresponding to one of front and rear waist regions, a second waist region (14) corresponding to the other of the front and rear waist regions and a crotch region (15) extending between the first and second waist regions, wherein at least one of the first and second waist regions as a whole, or in only its part adjacent a waist-opening (24), is elastic and formed of an inner sheet (30) defining the skin-facing side and an outer sheet (32) defining the non-skin-facing side and the non-skin-facing side of the outer sheet is formed substantially over its entire area with a plurality of thermocompression-bonded spots (20) regularly and intermittently arranged at intervals, wherein:

the outer sheet has non-thermocompressed regions (64) surrounded by the plurality of thermocompression-bonded spots;

the outer sheet is provided with a fibrous layer at least on the outer surface thereof and being formed of thermal adhesive crimped fibers (63);

the crimped fibers are bonded together by thermocompression-bonding treatment in the thermocompression-bonded spots;

the outer sheet and the inner sheet are bonded to each other by adhesive applied on at least one of respective opposite surfaces thereof; and the crimped fibers in the non-thermocompressed regions are arranged to protrude outward in a thickness direction of the outer sheet as the inner sheet contracts in the transverse direction.

The aspect of the present invention described in the above item (i) may provide one or more of the following advantageous effects:

(a) The crimped fibers are fusion-bonded or interlaced one with another only at the thermocompression-bonded spots and are neither fusion-bonded nor interlaced with one another, so as to be freely movable, in the non-thermocompressed regions surrounded by the thermocompression-bonded spots. In consequence, the crimped fibers in the non-thermocompressed regions of the outer sheet may follow the movement of the inner sheet, which is bonded to the outer sheet by adhesive, in response to contraction of the inner sheet; and the crimped fibers in the non-thermocompressed regions protrude outward as a distance between each pair of the adjacent thermocompression-bonded spots is reduced. As a result, the crimped fibers in the non-thermocompressed regions protrude further outward and become bulky, providing an airy and flexible texture.

Additionally, one or more of the following embodiments are provided in accordance with the following, preferred, further aspects, which may be taken alone or in combination with one another:

(ii) The inner sheet is elasticized and is bonded under tension in the transverse direction to the outer sheet by the adhesive (35).

(iii) The plurality of thermocompression-bonded spots are arranged in two directions to form a plurality of thermocompression-bonded lines and the thermocompression-bonded lines comprise rows of thermocompression-bonding lines extending at a first angle with respect to the transverse axis and columns of thermocompression-bonding lines extending at a second angle with respect to the transverse axis and intersecting with the rows of first thermocompression-bonding lines to create a plaid pattern.

(iv) The outer sheet is provided with a fibrous layer lying adjacent to the inner sheet and having non-crimped fibers as main material.

(v) The inner sheet comprises a blend fiber of a thermal adhesive elastomeric fiber and a thermal adhesive non-elastomeric fiber as a material.

(vi) The inner sheet has an outer layer (80) lying adjacent to the outer sheet and comprising blend fibers of thermal adhesive elastomeric fibers and thermal adhesive non-elastomeric fibers as a material and an inner layer (81) comprising a thermal adhesive elastomeric fiber as a material.

(vii) The front waist region formed of the outer sheet and the inner sheet exhibits a total luminous transmittance of 40% or lower as a whole, or a part only thereof, with the article put on a wearer's body.

(viii) The non-thermocompressed regions are formed in respective central zones thereof with two or more central thermocompression-bonded spots.

(ix) The crimped fibers in the non-thermocompressed regions are filament fibers.

(x) The inner sheet and the outer sheet are bonded to each other with the adhesive coated substantially evenly and intermittently in the transverse direction to define bonded regions and non-bonded regions so that, in the non-bonded regions, the outer sheet may protrude outward in a thickness direction of the outer sheet and space from the inner sheet to form voids (72) between the outer sheet and the inner sheet in response to contraction of the inner sheet in the transverse direction.

(xi) The adhesive is applied at a mass in the range of about 1.0 to about 5.0 $g/m^2$ in a plurality of bonding lines each of which has a width in a range of about 0.01 to about 0.1 mm.

(xii) An area percentage of the inner sheet covered by the adhesive versus the entire inner surface of the inner sheet is in a range of about 2 to about 10%.

(xiii) Each of the intervals at which the adhesive is applied in the transverse direction is smaller than a width dimension of the criss-cross pattern in the transverse direction.

(xiv) The the crimped fibers are separated one another, or at least partially separated one another, in the non-thermocompressed regions.

(xv) A bending stiffness and a bending restore property of the first waist region comprising the inner sheet and the outer sheet according to the KES method, in the transverse direction is 0.144 gf*$cm^2$/cm or less and is 0.16 gf*cm/cm or less, respectively.

(xvi) The adhesive is applied at a mass in the range of about 1.0 to about 5.0 $g/m^2$ in a plurality of bonding lines each of which has a width in a range of about 0.01 to about 0.1 mm.

(xvii) An area percentage of the inner sheet covered by the adhesive versus the entire inner surface of the inner sheet is in a range of about 2 to about 10%.

(xviii) The inner sheet is bonded under tension at a stretch ratio of 1.5 to 3.0 in the transverse direction to the outer sheet by the adhesive.

(xix) The outer sheet has an elastic stretch percentage in a range of 100 to 150% and the outer sheet has an elastic stretch percentage in a range of 150 to 300%.

(xx) The outer sheet is a thermal adhesive spun bonded non-woven fabric having a mass in a range of about 15 to 40 $g/m^2$ and a fiber density in the range a range of about 0.1 to 0.06 $g/cm^3$.

(xxi) The inner sheet is a non-woven fabric of thermal adhesive elastomeric fiber having a mass in a range of about 20 to 50 $g/m^2$ and a fiber density in a range of about 0.01 to 0.04 $g/cm^3$.

The crimped fiber has a fineness in a range of about 0.5 to 3.0 derniers and a about 5 to 25 crimps per 25 mm.

(xxii) The thermocompression-bonding lines intersect with each other to define a plurality of substantially rhombic non-thermocompressed regions.

(xxiii) The thermocompression-bonded spots are circular with a diameter in the range of about 0.4 to 0.8 mm.

(xxiv) An area percentage of the inner sheet covered by the adhesive versus the entire inner surface of the inner sheet is in a range of about 4 to about 6%.

(xxv) The adhesive is a hot melt adhesive.

(xxvi) A distance between each pair of the adjacent bonding lines is in a range of about 1.0 to about 2.5 mm. More preferably, in a range of about 1.5 to about 2.0 mm.

(xxvii) The plurality of bonding lines extend in the longitudinal direction and are spaced from one another in the transverse direction, each bonding line substantially comprising a continuous repeated pattern formed by alternating longitudinally and transversely extending line portions, wherein adjacent longitudinally extending line portions are spaced from one another in the transverse direction, and joined to one another, by a transverse extending line portion, and adjacent transversely extending line portions are spaced from one another in the longitudinal direction, and joined to one another, by a longitudinally extending line portion, and all of the bonding lines are in register with one another, such that all of the line portions of each bonding line lie parallel to corresponding line portions of all of the other bonding lines.

In addition to the advantageous effect (a), the aspects of the present invention described in the above items (ii)-(xi) may provide one or more of the following advantageous effects:

(b) As in item (iii), A plurality of thermocompression-bonded spots arranged in predetermined directions to form a plurality of thermocompression-bonding lines can provide the outer surface of the outer sheet with wrinkles along the thermocompression-bonding lines. These wrinkles create a quilt pattern which provides, in turn, a decorative appearance.

(c) As in item (iv), the fibrous layer defining the inner surface of the outer sheet primarily formed from the non-crimped fibers provides the outer sheet with a more flat surface than the sheet in which this fibrous layer is formed from the crimped fibers only. Such flat surface allows the outer sheet to be further stably bonded to the inner sheet by hot melt adhesive.

(d) As in item (v), the inner sheet formed from blend fibers of elastomeric fibers and non-elastomeric fibers may provide a good flexibility and a good texture compared favorably with the inner sheet formed from elastomeric fibers only.

(e) As in item (vi), the outer layer formed of blend fibers of elastomeric fibers and non-elastomeric fibers and lying on the side of the outer sheet can make the surfaces of the inner sheet and the outer sheet to be relatively flat allowing these two sheets to be stably bonded to each other.

(f) As in item (vii), the region defined by the inner sheet and the outer sheet having relatively low total luminous transmittance, specifically, of 40% or lower assures to eliminate a possibility that the wearer's body might be visually recognized from the exterior. Furthermore, such low total luminous transmittance makes it difficult to recognize visually a color difference between the region occupied by the absorbent structure and the region containing no absorbent structure and therefore the diaper has an outer appearance much like underwear compared to the conventional disposable diaper.

(g) As in item (viii), the central thermocompression-bonded spots formed in the central zone of the non-thermocompressed region can form an additional two or more protuberances which serve to improve flexibility of the sheet as a whole.

(h) As in item (ix), the continuous filament of the crimped fibers constituting the outer sheet which is partially compressed can maintain the sheet-like structure even when the respective adjacent thermocompression-bonded spots are spaced from by a given distance.

(i) As in items (x) through (xiii), the protuberances of the crimped fibers lying in the non-thermocompressed regions and the voids between the outer sheet and the inner sheet formed in response to contraction of the inner sheet provide the outer sheet with bulkiness and an airy and flexible texture.

(j) As in item (xiv), the crimped fibers in the non-thermocompressed regions at least partially not bonded one to another allow themselves to move freely so as to improve texture of the diaper's outer surface.

(k) As in item (xv), a bending stiffness and a bending restore property of one of the first waist region and the second waist region comprising the inner sheet and the outer sheet of the diaper is relatively small, therefore the one is easy to bend and has excellent restore property.

According to the embodiments in the above (ii) to (xv), the advantageous effect(s) set forth at (a)-(j) is/are better ensured. Further advantageous effects of the respective embodiments may be obtained as discussed in the respective related descriptions.

The terms "first" and "second" herein are used merely for distinguishing between similar elements. Furthermore, the wording "first waist region" herein means one of the front and rear waist regions, and the wording "second waist region" means the other.

The invention claimed is:

1. A disposable wearing article having a longitudinal axis extending in a longitudinal direction, a transverse axis orthogonal to said longitudinal axis and extending in a transverse direction, and comprising:
   a skin-facing side,
   a non-skin-facing side,
   a first waist region corresponding to one of front and rear waist regions,
   a second waist region corresponding to another of said front and rear waist regions, and
   a crotch region extending between said first and second waist regions,
   wherein
   at least one of said second and first waist regions as a whole, or in its part adjacent a waist-opening, is elasticized and formed of (i) an inner sheet defining said skin-facing side and (ii) an outer sheet defining said non-skin-facing side,
   said non-skin-facing side of said outer sheet is formed substantially over its entire area with a plurality of thermocompression-bonded spots regularly and intermittently arranged at intervals,
   said outer sheet has non-thermocompressed regions surrounded by said plurality of thermocompression-bonded spots,
   said outer sheet includes a fibrous layer at least on said outer surface thereof and being formed of thermal adhesive crimped fibers,
   said crimped fibers are bonded together by thermocompression-bonding treatment in said thermocompression-bonded spots,
   the crimped fibers are free of being thermocompression-bonded with each other in the non-thermocompressed regions,
   said outer sheet and said inner sheet are bonded to each other by adhesive applied on at least one of respective opposite surfaces thereof,
   said inner sheet is elasticized and is bonded under tension in said transverse direction to the outer sheet by the adhesive,
   said inner sheet includes an elastic fibrous non-woven fabric and is configured to directly contact a wearer's skin when the disposable wearing article is worn on the wearer,
   said crimped fibers in said non-thermocompressed regions are arranged to protrude outward in a thickness direction of said outer sheet as said inner sheet contracts in said transverse direction,
   said inner sheet and said outer sheet are bonded to each other with said adhesive coated substantially evenly and intermittently in said transverse direction to define
      bonded regions including the thermocompression-bonded spots and said adhesive, and
      non-bonded regions including the non-thermocompressed regions and free of said adhesive, and
   wherein the crimped fibers in the outer sheet are neither fusion bonded nor interlaced with each other in the non-thermocompressed regions such that in said non-bonded regions, said outer sheet protrudes outward in the thickness direction of said outer sheet and is spaced from said inner sheet, to form voids between said outer sheet and said inner sheet, in response to contraction of said inner sheet in said transverse direction.

2. The wearing article defined by claim 1, wherein said plurality of thermocompression-bonded spots are arranged in two directions to form a plurality of thermocompression-bonding lines and said thermocompression-bonding lines comprise:
   rows of thermocompression-bonding lines extending at a first angle with respect to said transverse axis, and
   columns of thermocompression-bonding lines extending at a second angle with respect to said transverse axis and intersecting with said rows of first thermocompression-bonding lines to create a criss-cross pattern.

3. The wearing article defined by claim 2, wherein each of intervals at which said adhesive is applied in said transverse direction is smaller than a width dimension of said criss-cross pattern in said transverse direction.

4. The wearing article defined by claim 2, wherein
   each of said non-thermocompressed regions is defined in a zone surrounded by the corresponding row of thermocompression-bonding line and the corresponding column of thermocompresssion-bonding line, and
   said zone includes at least two thermocompression-bonded spots.

5. The wearing article defined by claim 1, wherein said outer sheet includes a further fibrous layer lying adjacent to said inner sheet, and the further fibrous layer comprises non-crimped fibers as its main material.

6. The wearing article defined by claim 1, wherein
   said inner sheet that includes the elastic fibrous non-woven fabric is arranged in the rear waist region,
   said front waist region comprises a further inner sheet configured to not directly contact the wearer's skin, and
   the further inner sheet of the front waist region comprises a blend of thermal adhesive elastomeric fibers and thermal adhesive non-elastomeric fibers.

7. The wearing article defined by claim 1, wherein
said inner sheet that includes the elastic fibrous non-woven fabric is arranged in the rear waist region,
said front waist region comprises a further inner sheet configured to not directly contact the wearer's skin, and
said further inner sheet of the front waist region has
an outer layer lying adjacent to an outer sheet of the front waist region and comprising a blend of thermal adhesive elastomeric fibers and thermal adhesive non-elastomeric fibers, and
an inner layer consisting of only thermal adhesive elastomeric fibers.

8. The wearing article defined by claim 7, wherein the inner layer of said further inner sheet consists of only thermal adhesive elastomeric fibers.

9. The wearing article defined by claim 1, wherein said front waist region exhibits a total luminous transmittance of 40% or lower, as a whole, or in a part thereof.

10. The wearing article defined by claim 1, wherein said non-thermocompressed regions are formed in respective central zones thereof with two or more central thermocompression-bonded spots.

11. The wearing article defined by claim 1, wherein said crimped fibers in said non-thermocompressed regions are filament fibers.

12. The wearing article defined by claim 1, wherein the adhesive is applied at a mass in the range of about 1.0 to about 5.0 g/m$^2$ in a plurality of bonding lines each of which has a width in a range of about 0.01 to about 0.1 mm.

13. The wearing article defined by claim 1, wherein an area percentage of the inner sheet covered by the adhesive versus the entire inner surface of the inner sheet is in a range of about 2 to about 10%.

14. The wearing article defined by claim 1, wherein said crimped fibers are separated from one another, or at least partially separated from one another, in said non-thermocompressed regions.

15. The wearing article defined by claim 1, wherein a bending stiffness and a bending restore property of the first waist region comprising said inner sheet and said outer sheet, according to the KES method, in said transverse direction is 0.144 gf*cm$^2$/cm or less and is 0.16gf*cm/cm or less, respectively.

16. The wearing article defined by claim 1, wherein
said inner sheet extends across said at least one of said second and first waist regions in said transverse direction, and
said inner sheet is bonded to said skin-facing side of said outer sheet.

17. The wearing article defined by claim 1, wherein each of the voids continuously extends from one thermocompression-bonded spot to an adjacent thermocompression-bonded spot.

18. The wearing article defined by claim 1, wherein said inner sheet consists of an elastic fibrous non-woven fabric.

19. The wearing article defined by claim 1, wherein the outer sheet has a lower elastic stretch property than the inner sheet.

* * * * *